United States Patent [19]

Christensen et al.

[11] 4,374,848
[45] Feb. 22, 1983

[54] 6-(1-HYDROXYETHYL)CYCLONOCARDICIN

[75] Inventors: Burton G. Christensen, Cliffside Park; James V. Heck, Fanwood; Michael J. Szymonifka, Rahway, all of N.J.

[73] Assignee: Merck & Co., Inc., Rahway, N.J.

[21] Appl. No.: 301,544

[22] Filed: Sep. 14, 1981

[51] Int. Cl.³ .................... A61K 31/40; C07D 487/14
[52] U.S. Cl. .............................. 424/274; 260/245.2 R
[58] Field of Search .................. 260/245.2 R; 424/274

[56] References Cited

PUBLICATIONS

Aoki et al, The Journal of Antibiotics, May 1976, pp. 492–500.

*Primary Examiner*—Richard Raymond
*Attorney, Agent, or Firm*—James A. Arno; Hesna J. Pfeiffer

[57] ABSTRACT

Disclosed are 6-(1-hydroxyethyl)cyclonocardicins (I) and their pharmaceutically acceptable salts and esters which are useful as antibiotics.

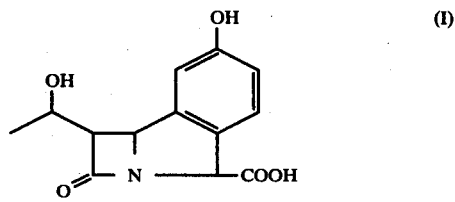

Also disclosed are processes for the preparation of such compounds; pharmaceutical compositions comprising such compounds; and methods of treatment comprising administering such compounds and compositions when an antibiotic effect is indicated.

3 Claims, No Drawings

6-(1-HYDROXYETHYL)CYCLONOCARDICIN

BACKGROUND OF THE INVENTION

This invention relates to 6-(1-hydroxyethyl)cyclonocardicins (I) and the pharmaceutically acceptable salt and ester derivatives thereof which are useful as antibiotics:

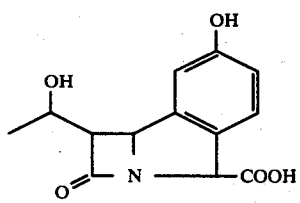

I

This invention also relates to the carboxyl derivatives of I which are antibiotics and which may be represented by the following generic structure (I):

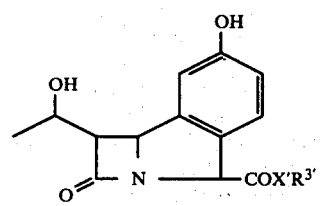

wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^{3'}$ may also be a readily removable blocking group. The definition of $R^{3'}$ is given in greater detail below.

This invention also relates to processes for the preparation of such compounds I; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inaminate systems. These antibiotics are active against a broad range of pathogens wich representatively include both Gram positive bacteria such as S. aureus, Strep. pyogenes, and B. subtilis, and Gram negative bacteria such as E. coli, Pseudomonas, Proteus morganii, Serratia, and Klebsiella. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

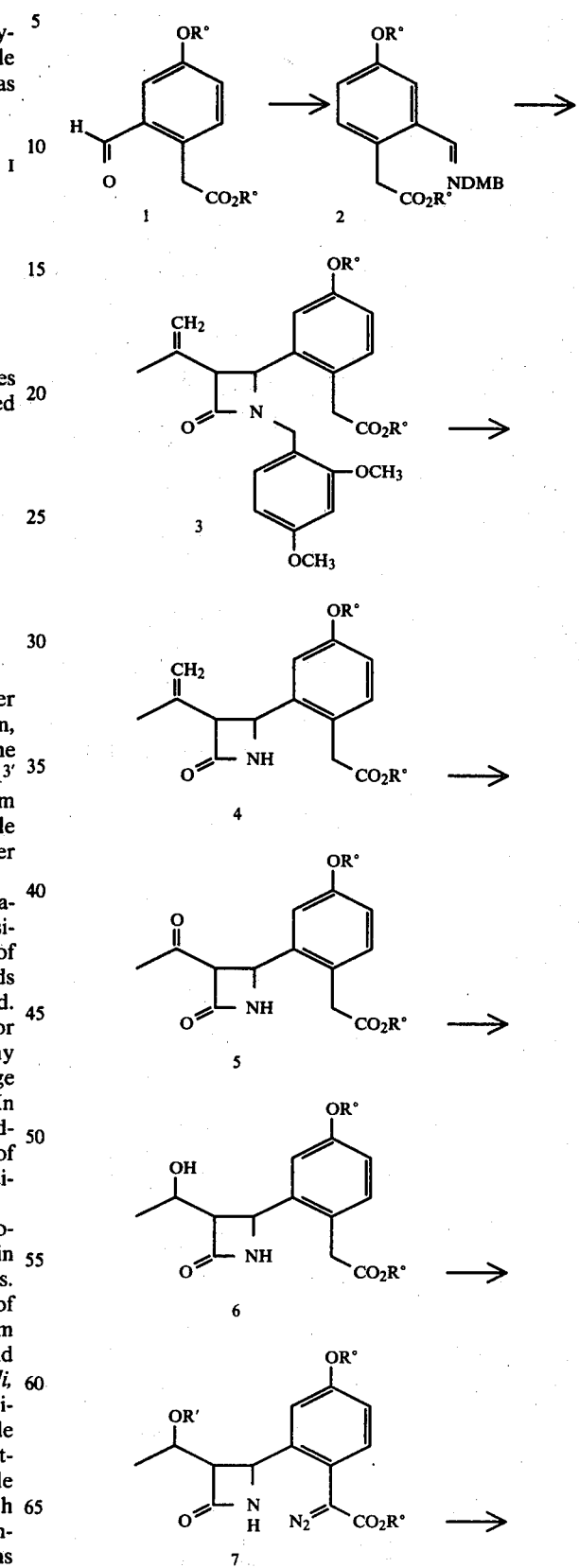

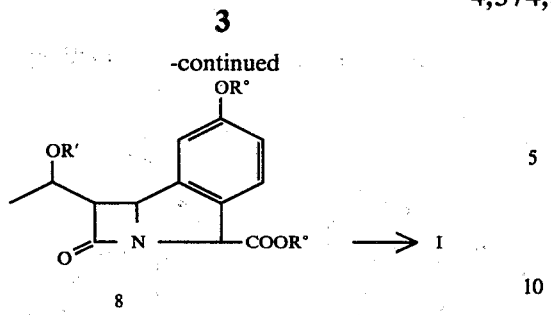

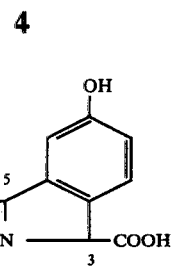

In words relative to the above diagram, treatment of the aldehyde (1) with 2,4-dimethoxybenzylamine and magnesium sulfate in dichloromethane affords imine (2). Relative to starting material 1, R° is a removable protecting group such as benzyl or the like. Dropwise addition of a solution of 3,3-dimethylacryloyl chloride (DMAC) to a solution of 2 and triethylamine in dichloromethane at 25° to 41° C. [method of Zamboni & Just, 57 Can. J. Chem. 1954 (1979)] yields 3. However, a study of this reaction revealed a remarkable temperature/solvent effect: substitution of refluxing chloroform for refluxing dichloromethane afforded 3 contaminated with only trace amounts of isomers and isolation in 86% yield could be effected by flash chromatography.

Oxidative hydrolysis of the dimethoxybenzyl group (3 to 4) is accomplished by exposure to 4 eq. potassium persulfate and 2 eg. dipotassium hydrogenphosphate in refluxing aqueous acetonitrile provides 4 in 46% yield.

Oxidative cleavage of the isopropylidene double bond (4 to 5) with catalytic osmium tetroxide and sodium periodate in aqueous pyridine provides the trans-3-acetyl derivative (5) in 88% yield, the initially formed cis ketone undergoing isomerization to the thermodynamically favored trans form under the reaction conditions.

Reduction of the acetyl group of 5 with 1.5 equivalents of sodium borohydride (6 equivalents hydride) in THF-isopropanol containing 1.0 eq. acetic acid at −60° C. affords a 3:4 mixture of isomeric alcohols 6 in 65% yield. Assignment of the RSR configuration to the major isomer of 6 is based upon the magnitude of the nmr vicinal coupling constant between the side-chain methine proton and the 3-proton of the azetidinone.

The transformation of 6 to the diazo ester 7 is achieved via silylation of 6 with bis(trimethylsilyl)trifluoroacetamide, chlorotrimethylsilane and 4-dimethylaminopyridine (BSTFA-TMSCl-DMAP) followed by treatment with p-nitro-benzenesulfonyl azide and LiOC(C₂H₅)₃ in THF at −60° to afford the unstable diazoester. Exposure of 7 to a catalytic amount of rhodium acetate in toluene at 80° affords 8 as a 2:1 mixture of endo- and exocarboxyl diastereomers which could not readily be separated by chromatography. However, when this mixture is subjected to hydrogenolysis (Pd(OH)₂, 1 atm H₂, 1.0 eg. 0.1 N KHCO₃, THF-EtOH-H₂O), the resulting RSR isomer and SSR isomer potassium salts of I are readily separated by reversed-phase tlc (Analtech RP plates, 20% aqueous methanol as eluant).

Compounds of the present invention having absolute configurations 3R, 5R, 6S, 8R and 3R, 5R, 6S, 8S are preferred:

As noted above, the compounds of the present invention may also generally be represented by the following structural formula:

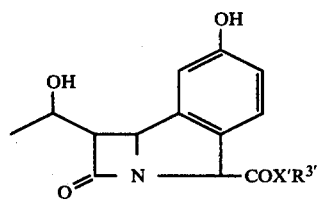

wherein X' is oxygen, sulfur or NR' (R' is hydrogen or loweralkyl having from 1 to 6 carbon atoms); and R³' is hydrogen, or, inter alia, is representatively selected to provide the pharmaceutically acceptable salt, ester, anhydride (R³' is acyl), and amide moieties known in the bicyclic β-lactam antibiotic art; R³' may also be a readily removable blocking group.

Identification of the Radical —COX'R³'

In the generic representation of the compounds of the present invention (I, above), the radical represented by —COX'R³' is, inter alia, —COOH (X' is oxygen and R³' is hydrogen) and all radicals known to be effective as pharmaceutically acceptable ester, anhydride (R³' is acyl) and amide radicals in the bicyclic β-lactam antibiotic art, such as the cephalosporins and penicillins and nuclear analogues thereof.

Suitable, but representative, blocking esters R³' (X=O) include those selected from the following list which is representative:

(i) R³'=CRᵃRᵇRᶜ wherein at least one of Rᵃ, Rᵇ, and Rᶜ is an electrondonor, e.g., p-methoxyphenyl. The remaining Rᵃ, Rᵇ and Rᶜ groups may be hydrogen or organic substituting groups. Suitable ester groups of this type include p-methoxybenzyloxycarbonyl.

(ii) R³'=CRᵃRᵇRᶜ wherein at least one of Rᵃ, Rᵇ and Rᶜ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) R³'=CRᵃRᵇRᶜ wherein at least two of Rᵃ, Rᵇ and Rᶜ are hydrocarbon such as alkyl, e.g., methyl or ethyl, or aryl, e.g., phenyl and the remaining Rᵃ, Rᵇ and Rᶜ group, if there is one, is hydrogen. Suitable esters of this type include t-butyloxycarbonyl, diphenylmethoxycarbonyl and triphenylmethoxycarbonyl.

Silyl esters. This category of blocking groups, may conveniently be prepared from a halosilane of the formula: R₃⁴SiX' wherein X' is a halogen such as chloro or bromo and R⁴ is alkyl, having 1–6 carbon atoms, phenyl, or phenylalkyl.

Pharmaceutically acceptable carboxyl derivatives of the present invention are those derived by reacting I with alcohols, acylating reagents and the like. For example, esters and amides of interest are the above-listed starting materials and final products having the —COX'R³' group at the 3-position; wherein X' is oxygen, sulfur or NR' (R' is H or R³'), and R³' is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkylportion has 1–6 carbon atoms, such as pivaloyloxymethyl; haloalkyl wherein halo is chloro, and the alkyl portion is straight or branched having 1–6 carbon atoms, e.g., 2,2,2-trichloroethyl; alkenyl having 1–4 carbon atoms such, as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8–10 carbon atoms such as benzyloxymethyl, and (4-nitro) benzyloxymethyl.

In addition to the esters (and thio esters) listed above, amides are also embraced by the present invention, i.e., wherein X' is the

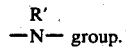

$$\overset{R'}{-N-} \text{ group.}$$

Representatives of such amides are those wherein R' is selected from the group consisting of hydrogen and alkyl such as methyl and ethyl.

The most preferred —COX'R³' radicals of the present invention are those wherein (relative to Structure I above), X' is oxygen and R³' is hydrogen; loweralkyl having 1–4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable antibiotics active against various Gram-positive and Gram-negative bacteria and accordingly find utility in human and veterinary medicine. Representative pathogens which are sensitive to antibiotics I include: *Straphylococcus aureus, Escherichia coli, Klebsiella pneumoniae, Bacillus subtilis, Salmonella typhosa Psuedomonas* and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above, schematic reaction diagram for the total synthesis of the defined cyclonocardicin antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

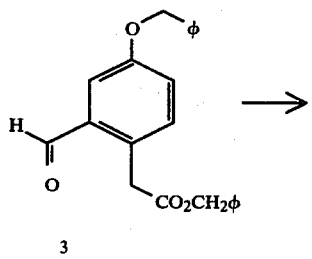

3

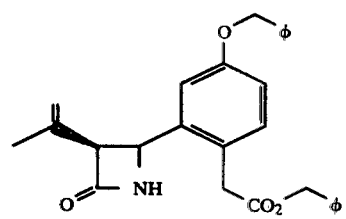

4

A mixture of aldehyde 3, 2,4-dimethoxybenzylamine (2.4 g) and magnesium sulfate (4.0 g) in 100 ml dichloromethane is stirred 4 hours at 25°, centrifuged and concentrated. The resulting crystalline imine is dissolved in 100 ml chloroform, 3.0 ml triethylamine added and the mixture brought to reflux. 3,3-dimethylacryloyl chloride (2.35 ml) in 20 ml chloroform is added dropwise over 20 min. and the solution refluxed one hour more. Workup with aqueous sodium bicarbonate followed by chromatography of the crude product on silica gel with ether-hexanes as eluant affords 6.9 g pure 4.

EXAMPLE 2

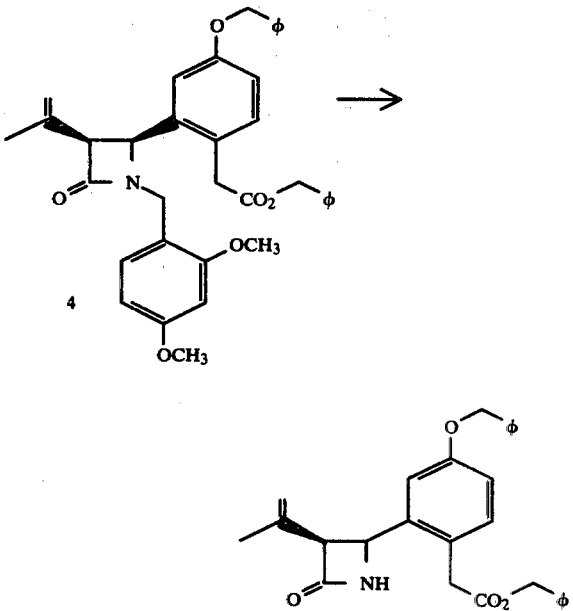

A mixture of (3) (1.05 g), potassium persulfate (1.83 g) and dipotassium hydrogen phosphate (0.60 g) is dissolved in 40 ml acetonitrile and 20 ml water and allowed to reflux at 90° for 1 hour. The resulting mixture is concentrated to one-half volume and partioned between chloroform and water. The organic phase is dried over sodium sulfate and concentrated to yield a crude product which is purified by chromatography on silica gel to yield pure 5 (0.36 g).

EXAMPLE 3

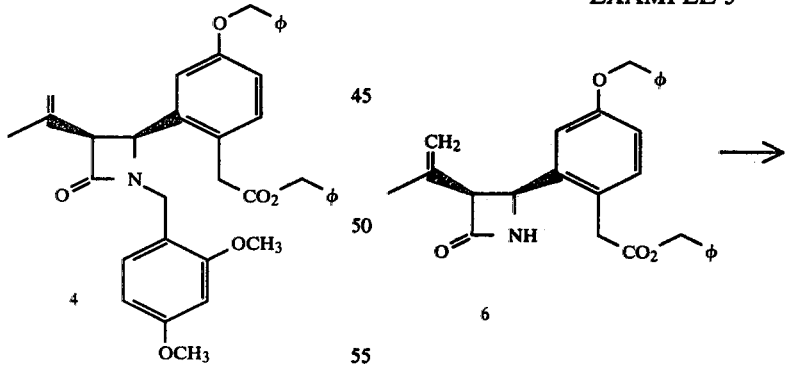

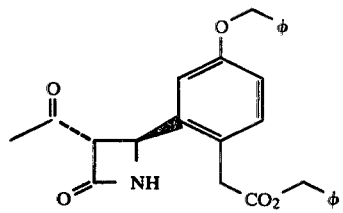

7

The olefin (6) (1.00 g) is dissolved in a mixture of 40 ml ether and 5 ml dichloromethane and finely-ground sodium periodate (2.44 g) 20 ml water, 0.2 ml pyridine and 0.5 ml of 0.5 m osmium tetroxide in toluene are added. A catalytic amount (5 mg) of te abutylammonium bisulfate is added and the mixture stirred at room temperature for 2.5 hours. The resulting mixture is partioned between 180 ml chloroform and 30 ml water and the organic phase washed with aqueous sodium bisulfate, dried over sodium sulfate and evaporated to yield a crude product. Purification is effected by chromatography on silica gel to yield pure trans-ketone (7) 0.87 g.

EXAMPLE 4

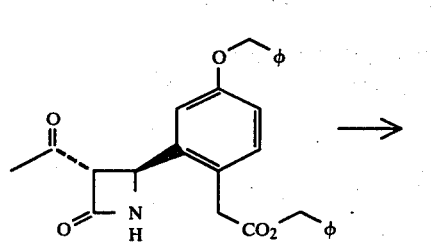

7

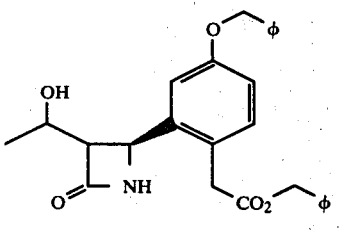

7R

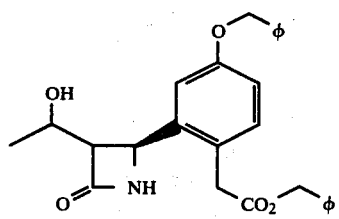

7S

A solution of ketone (7) (2.23 g) and acetic acid (0.28 ml) in 100 ml dry THF is cooled to −60° and a solution of sodium borohydride (0.1 m in iPrOH, 76 ml) is added dropwise after 15 min. The solution is allowed to warm to −30° over 1 hour then quenched with 20 ml pH 4 phosphate buffer. The mixture is partioned between 250 ml chloroform and 100 ml water and the organic phase is washed with aq. sodium bicarbonate and brine, dried over sodium sulfate and evaporated to yield a mixture of alcohols 7S and 7R. The diastereomers are separated by chromatography on silica gel with ethylacetate-dichloromethane as eluant (ratio 7R:7S is 4:3).

EXAMPLE 5

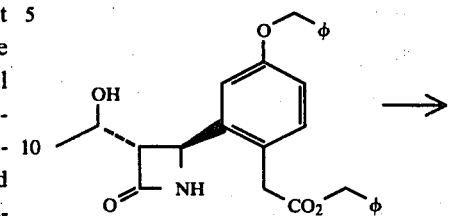

9

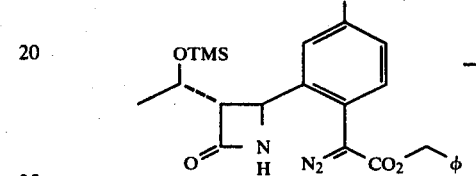

10

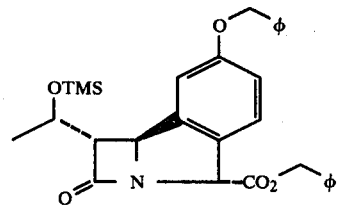

11

A solution of alcohol 9 (0.656 g), bis(trimethylsilyl)-trifluoroacetamide (1.6 ml), chlorotrimethylsilane (0.18 ml) and 4-dimethylaminopyridine (1 mg) in 15 ml acetonitrile is kept at room temperature for 18 hours. The mixture is co-evaporated three times with dry toluene and pumped at 0.1 mm 18 hours to yield crude disilyl compound. A portion of this material (213 mg) is combined with o-nitrobenzenesulfonyl azide (164 mg) in 4 ml THF and cooled to −40°. A solution of lithium triethylcarboxide (1.6 M, 0.248 ml) is added dropwise over 1 min. and the solution allowed to warm to −10° over 45 min. The mixture is cooled to −78°, diluted with 10 ml toluene and quenched with pH 7 buffer. The organic phase is separated dried over potassium carbonate and evaporated at 0° in high vacuum to yield crude diazo compound 10. Purification is effected by low temperature chromatography on silica gel. (ir 2080 cm$^{-1}$). Diazoester 10 (30 mg) is dissolved in 2.0 ml degassed toluene and 1 mg rhodium (II) acetate is added. The mixture is heated to 80° for 30 min. and then evaporated in vacuo. The residue is chromatographed on silica gel to yield cyclonocardicin 11.

EXAMPLE 6

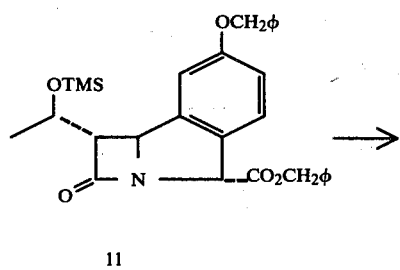

11

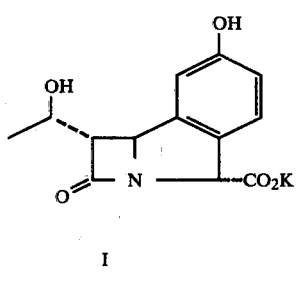

I

Cyclonocardicin ester 11 (5 mg) is dissolved in 1.0 ml THF and cooled to 0°. A mixture of 0.2 ml water, 0.2 ml ethanol and 0.08 ml 0.1 M potassium bicarbonate is added, followed by 5 mg of 20% palladium hydroxide. The mixture is stirred under 1 atm. of hydrogen at 0° for 2 hours, diluted with 1.5 ml water and concentrated to one-half volume at 0°. Isolation of (I) is effected by reversed-phase chromatography on Analtech thin-layer plates.

EXAMPLE 7

Preparation of Pharmaceutical Compositions

One such unit dosage form is prepared by mixing 120 mg of compound A (compound of Example 6) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water | to 1 ml. |
| OTIC SOLUTION | |
| Compound A | 100 mg. |
| Benzalkonium chloride | 0.1 mg. |
| Sterile Water | to 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:
1. A compound of the structure:

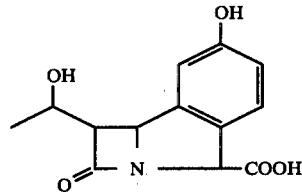

and the pharmaceutically acceptable salts and esters.
2. An antibiotic method of treatment comprising administering a therapeutically effective amount of a compound according to claim 1.
3. An antibiotic pharmaceutical composition comprising a therapeutically effective amount of a compound according to claim 1 and a carrier therefor.

* * * * *